US00PP16904P3

(12) United States Plant Patent
Danziger

(10) Patent No.: US PP16,904 P3
(45) Date of Patent: Aug. 1, 2006

(54) **NEW GUINEA *IMPATIENS* PLANT NAMED 'DANHARPURCROWN'**

(50) Latin Name: *Impatiens hawkeri*
Varietal Denomination: Danharpurcrown

(75) Inventor: Gabriel Danziger, Moshav Nir-Zvi (IL)

(73) Assignee: Danziger "Dan" Flower Farm, Post Beit Dagan (IL)

( * ) Notice: Subject to any disclaimer, the term of this patent is extended or adjusted under 35 U.S.C. 154(b) by 88 days.

(21) Appl. No.: 10/846,634

(22) Filed: May 17, 2004

(65) Prior Publication Data

US 2005/0257306 P1 Nov. 17, 2005

(51) Int. Cl.
*A01H 5/00* (2006.01)

(52) U.S. Cl. ..... Plt./318

(58) Field of Classification Search ..... Plt./318
See application file for complete search history.

*Primary Examiner*—Kent Bell
*Assistant Examiner*—Louanne Krawczewicz Myers
(74) *Attorney, Agent, or Firm*—Foley & Lardner LLP

(57) ABSTRACT

A new and distinct *Impatiens* plant named 'Danharpurcrown' characterized by having large, round flowers, bicolor purple flower color; green leaves, mature leaf upper surface RHS 147 A; and compact and round plant habit.

2 Drawing Sheets

Genus and species of the plant claimed: *Impatiens hawkeri.*

Variety denomination: 'Danharpurcrown'.

BACKGROUND OF THE INVENTION

The present invention relates to a new and distinct cultivar of New Guinea *Impatiens* plant, botanically known as *Impatiens,* hereinafter referred to by the cultivar name 'Danharpurcrown'.

The new cultivar originated from a cross made in a controlled breeding program made by the inventor, Gabriel Danziger, in 1999 in Moshav Mishmar Hashiva, Israel. The female parent is a proprietary cultivar designated E-703 (unpatented). The male parent is a proprietary cultivar designated E-110 (unpatented). 'Danharpurcrown' was discovered and selected by the inventor, Gabriel Danziger, as a flowering plant within the progeny of the stated cross in a controlled environment in Moshav Mishmar Hashiva, Israel.

Asexual reproduction of the new cultivar was performed by leaf cuttings. The cuttings are apical cuttings; no more than two expanded leaves and three to four immature leaves evident. Asexual reproduction of 'Danharpurcrown' was first performed December, 2000, in Moshav Mishmar Hashiva, Israel, and has demonstrated that the combination of characteristics as herein disclosed for the new cultivar are firmly fixed and retained through successive generations of asexual reproduction. The new variety is stable and reproduces true to type in successive generations of asexual reproduction.

BRIEF DESCRIPTION OF THE INVENTION

The following traits have been repeatedly observed and are determined to be basic characteristics of 'Danharpurcrown' which in combination distinguish this *Impatiens* as a new and distinct cultivar:

1. Large, round flower;
2. bicolor purple flower color;

3. green leaves, mature leaf upper surface RHS 147A; and
4. compact and round plant habit.

'Danharpurcrown' has not been observed under all possible environmental conditions. The phenotype of the new cultivar may vary significantly with variations in environment such as temperature, light intensity, and daylength without any change in the genotype of the plant. The following observations, measurements and values describe the new cultivar as grown in Moshav Mishmar Hashiva, Israel, under conditions which closely approximate those generally used in commercial practice.

Plants of the new *Impatiens* cultivar 'Danharpurcrown' differ from plants of the parents, 'E-703' (unpatented) and 'E-110' (unpatented), in the following characteristics described in Table 1:

TABLE 1

| Trait | New Cultivar 'Danharpurcrown' | Female Parent 'E-703' (unpatented) | Male Parent 'E-110' (unpatented) |
|---|---|---|---|
| Flower color | Bi-color purple, RHS 66A and RHS 80A | Bi-color purple RHS 63A and RHS 80B | Red, RHS 42A |
| Plant Size | Height: 15 cm Width: 30 cm | Height: 20 cm Width: 30 cm | Height: 18 cm Width: 30 cm |

Of the many commercial cultivars known to the inventor, the most similar in comparison to 'Danharpurcrown' is cultivar 'Harmony Dark Betio' (unpatented). 'Danharpurcrown' has larger flowers than 'Harmony Dark Betio' and the flower color of 'Danharpurcrown' is darker than that of 'Harmony Dark Betio'.

BRIEF DESCRIPTION OF THE DRAWINGS

The accompanying photographic drawing show colors as true as is possible with reproductions of this nature. The first photograph shows a top view perspective of a 'Danharpurcrown' plant. The second photograph shows a close-up view of a flower, leaves and bud of 'Danharpurcrown'.

DETAILED BOTANICAL DESCRIPTION

The following observations, measurements and values describe the new cultivar as grown in Moshav Mishmar Hashiva, Israel, under conditions which closely approximate those generally used in commercial practice: day temperature ranging from 20° C. to 24° C., night temperature ranging from 18° C. to 20° C.; fertilized up to a level of 150–200 ppm N, 80 ppm P, and 150 ppm K. Color references are made to The Royal Horticultural Society Colour Chart (R.H.S.), except where general colors of ordinary significance are used. Color values were taken under daylight conditions at approximately 1:00 pm in a greenhouse. The age of the plant described is 12 weeks.

Plant:

*General appearance and form.*—Height: About 15 cm. Width: About 30 cm.

*Habit.*—Round and compact, very good branching.

*Flowering response.*—10–12 weeks after planting of rooted cuttings to finished product in 12 to 13 cm pots.

*Flowering season.*—All year round.

*Winter hardiness.*—Sensitive to temperatures below 10° C.

*Lastingness of the individual bloom.*—Floral life ranged 5–10 days after anthesis.

*Rooting.*—Time to initiate roots: 7–10 days in summer time (25° C.), 10–14 days in winter (20° C.); no hormone require for rooting.

*Fragrance.*—None.

Foliage:

*Size.*—Length: About 10–12 cm. Width: About 4–5 cm.

*Overall shape of leaf.*—Lanceolate ovate.

*Base shape.*—Acuminate.

*Tip shape.*—Attenuate.

*Margin.*—Denticulate.

*Texture.*—Smooth.

*Main color of upper surface.*—Mature leaf: Yellow-green, RHS 147 A. Immature leaf: Green, RHS 137 B.

*Main color of lower surface.*—Mature leaf: Green, RHS 138 B. Immature leaf: Green, RHS 138 B.

*Venation color.*—Upper surface: Red purple group, RHS 59 C. Lower surface: Red purple group, RHS 59 B.

*Petiole.*—Length: About 1 cm. Diameter: About 2 mm. Texture: Smooth. Color: Greyed-Purple Group, RHS 185A.

Inflorescence:

*Corolla.*—Form: Single. Shape: Round. Average Number of blooms: 20–25 flowers per mature plant [4 months old]. Diameter: Observed: 7–7.5 cm; Typical: 7–8 cm. Depth: Observed: 3 cm; Typical: 0.2–0.5 cm.

*Petal.*—Petal number: 5. Petal overall shape: Obcordate. Apex shape: Obcordate. Base shape: Acute. Length: Observed: 3.5 cm; Typical: 3–4 cm. Width: Observed: 3 cm; Typical: 3–3.5 cm. Margin: Entire.

*Petal color.*—Upper surface: Red purple group, RHS 66A to RHS 80A. Lower surface: Purple violet group, RHS 80C.

*Stem.*—Average length: About 13 cm. Average diameter: About 0.5 cm. Color: Red Purple group, RHS 59A. Internode length: About 4 cm.

*Spur.*—Quantity: Observed: 1; Typical: 1. Shape: Falcate. Length: Observed: 5.3 cm; Typical: 5.3 cm. Diameter: Observed: 1 mm; Typical: 1 mm. Aspect: 40° to 45° from peduncle. Color: Red purple, RHS 59B.

*Bud.*—Response: 10–14 days. Color: Red-Purple, RHS 61B. Length (before opening): About 2 cm. Diameter: At Apex: About 0.5 cm. At Base: About 1 cm. Shape: Ovate.

*Peduncle.*—Appearance and angle: Erect, 90° from corolla. Length: About 5.5 cm. Diameter: About 1 mm. Texture: Smooth. Strength: Stable. Color: Red purple group, RHS 60A.

Reproductive organs:

*Androecium.*—Stamen: Quantity: 1 per flower; white in color. Anthers: Color: RHS 63A, red purple group. Pollen: White, moderate amount.

*Gynoecium.*—Pistil: Quantity: one per flower; length: 3 mm; color: green, RHS 143B. Stigma: Nearly white, closest to RHS 157 D. Ovary: Light green, RHS 143 B.

*Seeds.*—Smooth; width 1 mm; length 2–3 mm; shape elliptic; brown in color (Greyed-Orange group), RHS 177A.

*Fruit.*—Explosive capsule; green in color RHS 141 D.

Disease/pest resistance/susceptibility: Not tested; no information currently available.

I claim:

1. A new and distinct New Guinea *Impatiens* plant named 'Danharpurcrown', as illustrated and described herein.

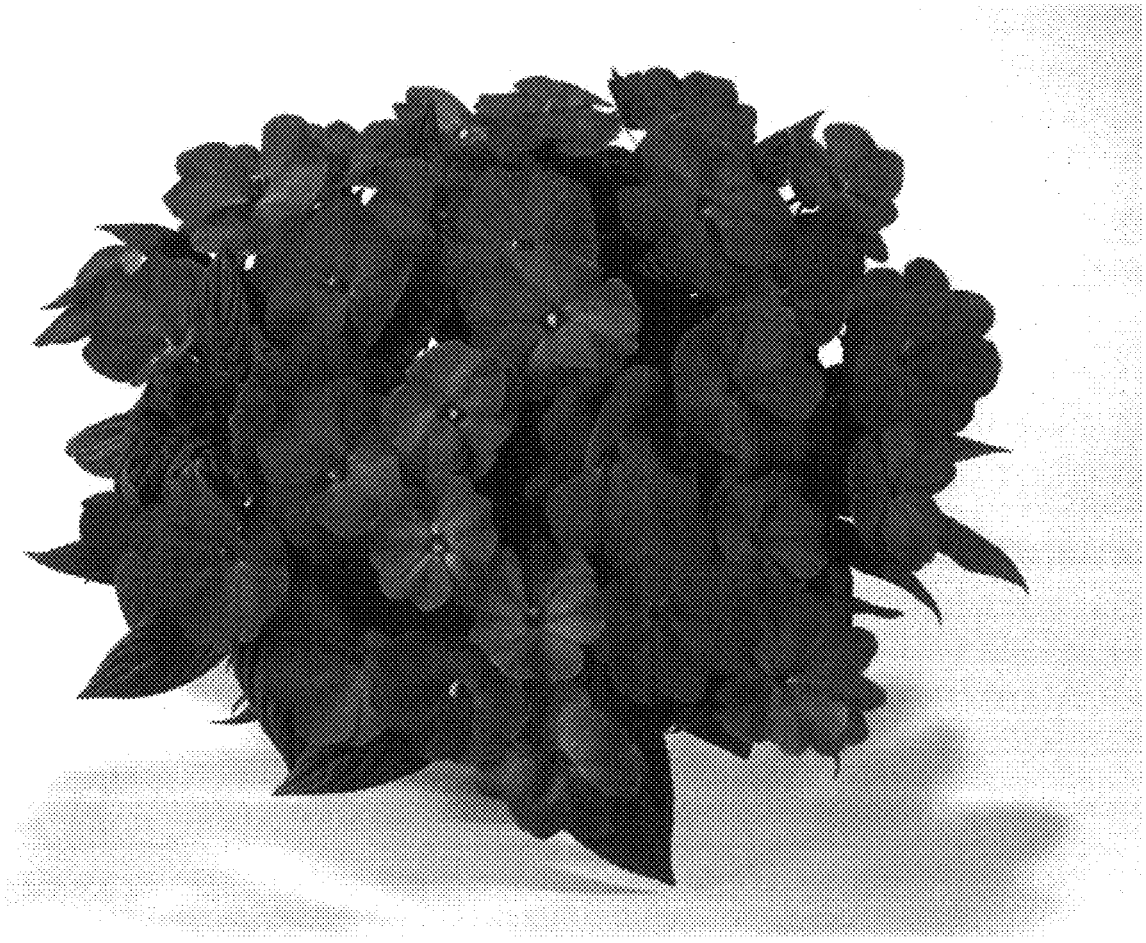

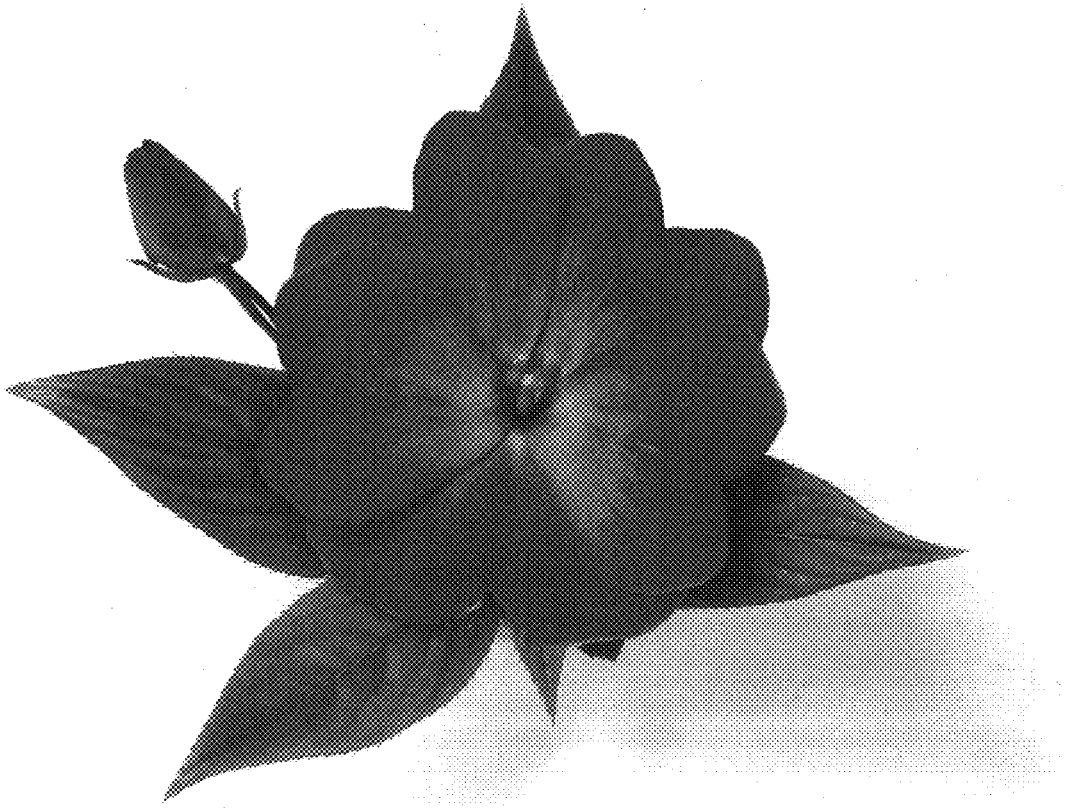

* * * * *